United States Patent [19]
Geibel et al.

[11] Patent Number: 6,051,720
[45] Date of Patent: Apr. 18, 2000

[54] REMOVAL OF CONTAMINANTS FROM N-METHYL-2-PYRROLIDONE

[75] Inventors: Jon F. Geibel; Richard A. Green, both of Bartlesville, Okla.

[73] Assignee: Phillips Petroleum Company, Bartlesville, Okla.

[21] Appl. No.: 09/330,638

[22] Filed: Jun. 11, 1999

[51] Int. Cl.⁷ .............................................. C07D 207/267
[52] U.S. Cl. .......................................................... 548/555
[58] Field of Search ............................................. 548/555

[56] References Cited

U.S. PATENT DOCUMENTS 4,501,902  2/1985  Cleary ..................................... 548/555
4,510,316  4/1985  Cleary et al. ........................... 548/444
4,895,959  1/1990  Kato et al. .............................. 548/555

*Primary Examiner*—Fiona T. Powers
*Attorney, Agent, or Firm*—Polly C. Owen

[57] ABSTRACT

A process is provided for moving at least one contaminant selected from the group consisting of phenol thiophenol, and phenyl disulfide from contaminated NMP by reacting at least one monohalogenated aromatic compound and a base with the contaminate NMP.

10 Claims, No Drawings

REMOVAL OF CONTAMINANTS FROM N-METHYL-2-PYRROLIDONE

FIELD OF INVENTION

This invention relates to the field of processes for removing at least one contaminant selected from the group consisting of phenol, thiophenol, and phenyl disulfide from contaminated NMP.

BACKGROUND OF THE INVENTION

NMP can be utilized in various chemical processes. For example, NMP is used as a reactant, chemical reaction medium, recrystallization medium, or a cleaning agent. NMP is often used as a chemical reaction medium since it has excellent heat and chemical stability.

In particular, NMP can be used in the production of poly(arylene sulfide), hereinafter referred to as P(AS). Generally, to produce P(AS), at least one halogenated aromatic compound, at least one sulfur source, and NMP are contacted under polymerization conditions. During the production of P(AS), at least one contaminant selected from the group consisting of phenol, thiophenol and phenyl disulfide can be generated producing a contaminated NMP. If the contaminated NMP is utilized in a subsequent polymerization, the P(AS) produced can have a significant reduction in molecular weight compared to P(AS) produced with uncontaminated NMP.

In addition, phenol, thiophenol and phenyl disulfide are difficult to separate from contaminated NMP. Distillation of the contaminated NMP is not sufficient to separate the phenol, thiophenol and phenyl disulfide from the NMP.

Polyhalogenated aromatic compounds have been utilized to remove thiophenol and phenyl disulfide from NMP. However, after an uncontaminated NMP is recovered, various compounds remain including unreacted aryl halides, which can cause a waste disposal problem.

There is a need in the industry to provide an efficient process to remove at least one contaminant from contaminated NMP that does not create waste disposal problems. This invention provides such a process.

SUMMARY OF THE INVENTION

It is an object of this invention to provide a process to remove at least one contaminant selected from the group consisting of phenol, thiophenol, and phenyl disulfide from contaminated NMP.

In accordance with this invention, a process is provided for removing at least one contaminant from contaminated NMP, said process comprising:

1) reacting at least one monohalogenated aromatic compound and at least one base with contaminated NMP to produce a first stream;
   wherein said monohalogenated aromatic compound is represented by the formula:

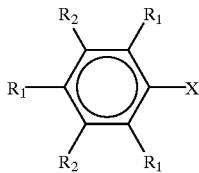

where X is a halogen;
where at least one $R_1$ constituent is an electron withdrawing radical and the remaining $R_1$ constituents are the same or different and are selected from the group consisting of hydrogen and hydrocarbyl radicals having from 1 to about 10 carbon atoms per radical;
where said $R_2$ constituents are the same or different and are selected from the group consisting of hydrogen and hydrocarbyl radicals having from 1 to about 10 carbon atoms per radical;
wherein said contaminated NMP contains at least one contaminant selected from the group consisting of phenol, thiophenol and phenyl disulfide;

2) heating said first stream to a temperature in the range of about 100° C. to about 300° C.; and 3) separating said first stream to produce a NMP-rich stream and a NMP-lean stream;
   wherein said NMP-rich stream comprises NMP;
   wherein said NMP-lean stream comprises reaction products of said contaminant, said monohalogenated aromatic compound, and said base.

These objects and other objects of this invention will become more apparent with reference to the following.

DETAILED DESCRIPTION OF INVENTION

A process is provided to remove at least one contaminant from contaminated NMP. Step 1 is reacting at least one monohalogenated aromatic compound and at least one base with contaminated NMP to produce a first stream.

Said monohalogenated aromatic compound, which can be used in the present invention, is represented by the formula:

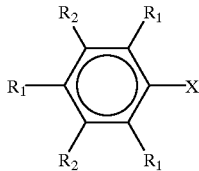

where X is a halogen;
where at least one $R_1$ constituent is an electron withdrawing radical and the remaining $R_1$ constituents are selected from the group consisting of hydrogen and hydrocarbyl radicals having from 1 to about 10 carbon atoms per radical;
where said $R_2$ constituents are the same or different and are selected from the group consisting of hydrogen and hydrocarbyl radicals having from 1 to about 10 carbon atoms per radical.

Any electron withdrawing radical capable of removing electron density from the aromatic ring in said monohalogenated aromatic compound can be used in this invention. Electron withdrawing radicals can be selected from the group consisting of:

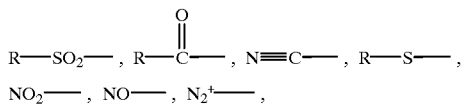

where R is selected from the group consisting of hydrocarbyl radicals having from 1 to about 20 carbons atoms per radical. Preferably, said monohalogenated aromatic compound can be selected from the group consisting of 4-chlorophenylsulfone, 4-chlorophenylbiphenylsulfone, 2-chlorophenylsulfone, 4-chlorobenzonitrile, 4-chlorobenzophenone, and p-nitrochlorobenzene.

The amount of said monohalogenated aromatic compound used is that which is sufficient in the presence of base to remove the contaminant. Generally, the amount of said monohalogenated aromatic compound ranges from about 1 mole per mole of said contaminant to about 5 moles per mole of said contaminant. Preferably, the amount of the monohalogenated aromatic compound ranges from about 1 mole per mole of said contaminant to about 3 moles per mole of said contaminant. If the amount of said monohalogenated aromatic compound is less than about 1 mole per mole of said contaminant, the contaminant may not be removed adequately from the contaminated NMP. If the amount of said monohalogenated aromatic compound is greater than 5 moles per mole of said contaminant, the process may not be economical since the cost of removing said contaminant from the contaminated NMP can be greater than purchasing virgin NMP. In addition, if said monohalogenated aromatic compound remains in said NMP-rich stream, the monohalogenated aromatic compound can inhibit the formation of high molecular weight P(AS).

Suitable bases for use in this invention are those strong enough to remove a proton from thiophenol. The base can be selected from the group consisting of alkali metal hydroxides and alkali metal carbonates. Alkali metal hydroxides can be selected from the group consisting of lithium hydroxide, sodium hydroxide, potassium hydroxide, rubidium hydroxide, cesium hydroxide, and mixtures thereof. Alkali metal carbonates can be selected from the group consisting of lithium carbonate, sodium carbonate, potassium carbonate, and mixtures thereof. The base can be added in the form of a solid or an aqueous solution.

The amount of the base to be used generally ranges from about 0.5 moles per mole of said contaminant to about 5 moles per mole of said contaminant. Preferably, the amount of the base to be used ranges from about 0.9 moles per mole of said contaminant to about 3 moles per mole of said contaminant. If the amount of base is less than 0.5 moles per mole of said contaminant, the contaminant may not be removed adequately from the contaminated NMP. If the amount of base is greater than 5 moles per mole of said contaminant, the process may not be economical.

Contaminated NMP contains at least one contaminant selected from the group consisting of phenol, thiophenol and phenyl disulfide. Generally, the contaminated NMP can be generated from any process. More particularly, the contaminated NMP is generated from the production of P(AS).

Said monohalogenated aromatic compound and base can be contacted with the contaminated NMP by any means known in the art. Contact time is that which is sufficient to react the monohalogenated aromatic compound, base, and the contaminated NMP. Generally, the contact time ranges from about 1 minute to about 10 hours.

Step 2 is heating said first stream to a sufficient temperature to convert said contaminant to compounds that can be separated from the NMP. The temperature to which said first stream is heated varies depending on the type of said monohalogenated aromatic compound utilized. In general, said first stream is heated to a temperature in the range of about 100° C. to about 300° C. Preferably, said first stream is heated to a temperature in the range of about 150° C. to about 270° C. Temperatures below 100° C. result in an increase in the time required to convert the contaminant to compounds that can be separated from NMP. Temperatures higher than 300° C. can cause decomposition of the NMP. Generally, the heating is conducted at atmospheric pressure, however, super-atmospheric or sub-atmospheric pressures are also permissible.

Step 3 is separating the first stream to produce the NMP-rich stream and the NMP-lean stream. The NMP-rich stream comprises NMP. The NMP-lean stream comprises the reaction products produced from said contaminant and monohalogenated aromatic compound. The separation can be achieved by any means known in the art. For example, separation can be effected by distillation equipment, such as, but not limited to, atmospheric pressure distillation equipment and vacuum distillation equipment.

EXAMPLES

Example 1

The purpose of this experiment was to determine if thiophenol and phenyl disulfide can be removed from contaminated NMP that has not been dehydrated prior to contacting said monohalogenated aromatic compound with the contaminated NMP.

650 grams of contaminated NMP, 21.67 grams of 4-chlorobenzophenone, and 32.51 grams of sodium carbonate were charged to a 1 liter stainless steel reactor. The reactor was degassed with 5 pressure and release cycles using 50 psig nitrogen and 5 pressure and release cycles using 200 psig nitrogen. The reactor was heated to 250° C. and held for 1.5 hours before cooling to room temperature.

The dehydration outlet of the reactor was opened to depressure the reactor. Then, a nitrogen purge was started through the reactor at a flowrate of 32 ml/min. The reactor was heated slowly to approximately 205° C. Samples of a NMP-rich stream comprising NMP were collected from the dehydration outlet. The reactor was then heated to approximately 212–214° C. Further samples of said NMP-rich stream were collected.

Samples of said NMP-rich stream collected at the beginning and the end of the experiment were analyzed by gas chromatography to determine the amount of thiophenol and phenyl disulfide remaining. The gas chromatography analyses did not detect any thiophenol or phenyl disulfide.

Example 2

The purpose of this experiment was to determine if said NMP-rich stream generated in Example 1 containing a large amount of water can be utilized to produced poly(phenylene sulfide), hereinafter referred to as PPS.

While under nitrogen purge, 1 mole of sodium hydrosulfide solution containing 58.77% by weight sodium hydrosulfide, 1.0027 moles of 98.3% by weight sodium hydroxide, 0.60 moles of anhydrous sodium acetate, and 2.5 moles of said NMP-rich stream recovered in Example 1 were charged to a 1 liter titanium reactor. The reactor was degassed with 5 pressure and release cycles using 50 psig nitrogen and 5 pressure and release cycles using 200 psig nitrogen. The reactor was heated to remove water. 0.9898 moles of p-dichlorobenzene and 1 mole of NMP were then charged to the reactor. The charge vessel was rinsed with 49.565 grams of NMP, and then it was charged to the reactor.

The reactor was heated to 235° C. and held for 1 hour. Then, the reactor was heated to 260° C. and held for 30 minutes. The reactor temperature was gradually raised to 265° C. for a total of 2 hours from the time that 260° C. was reached. 10 milliliters of NMP were charged to the reactor, and the temperature of 260° C. was held for an additional 30 minutes. The reactor was then cooled to room temperature before opening. A crude PPS product was removed from the reactor and washed with water to remove NMP and soluble salts to produce a PPS product. The PPS product was dried to constant weight in a vacuum oven at approximately 100° C.

The melt flow index of the PPS product produced was 576.04 g/10 minutes. The melt flow index was determined by the method of ASTM D 1238-86, Procedure B—Automatically Time Flow Rate Procedure, Condition 316/5.0 modified utilizing a 5 kg weight and 315° C., with the values of melt flow expressed in units of grams per 10 minutes. The melt flow index is indicative of the molecular weight of the polymer. A low melt flow indicates higher molecular weight polymer.

Example 3

The purpose of this experiment was to determine if thiophenol and phenyl disulfide can be removed from contaminated NMP that has been dehydrated prior to contacting said monohalogenated aromatic compound with the contaminated NMP.

Sodium hydroxide pellets were added to approximately 655 grams of contaminated NMP until the pH reached about 10 to produce a pH adjusted, contaminated NMP. The pH adjusted, contaminated NMP was added to a 1 liter stainless steel reactor. The reactor was degassed with 5 pressure and release cycles using 50 psig nitrogen and 5 pressure and release cycles using 200 psig nitrogen. The reactor was heated slowly to about 200° C. while being purged with nitrogen. The water was removed from a dehydration outlet.

21.67 grams of 4-chlorobenzophenone were dissolved in 100 grams of virgin NMP in a charge vessel and then charged to the reactor. 50 grams of virgin NMP were used to rinse the charge vessel, and it was then charged to the reactor. The reactor was heated to 250° C. and held for 3 hours. The reactor was then cooled to room temperature while under nitrogen pressure of about 188 psig.

The reactor was depressured by opening the dehydration outlet. The reactor was heated slowly to 110° C., and the dehydration outlet was opened. A nitrogen flow of 32 ml/min was started through the reactor. At about 205° C., a NMP-rich stream began to flow through the dehydration outlet, and samples were collected. When the flow of said NMP-rich stream became slow, 100 psig of nitrogen was added to the reactor, and the reactor was cooled to room temperature.

Samples of said NMP-rich stream collected at the beginning and the end of the experiment were analyzed by gas chromatography to determine the amount of thiophenol and phenyl disulfide remaining. The gas chromatography analyses did not detect any thiophenol or phenyl disulfide.

Example 4

Said NMP-rich stream obtained in Example 3 was used in a polymerization to produce PPS. The procedure described in Example 2 was followed. PPS having a melt flow index of 419.5 g/10 minutes was obtained.

That which is claimed is:

1. A process of removing at least one contaminant from contaminated N-methyl-2-pyrrolidone, said process comprising:

1) contacting at least one monohalogenated aromatic compound and at least one base with contaminated N-methyl-2-pyrrolidone to produce a first stream;
wherein said monohalogenated aromatic compound is represented by the formula:

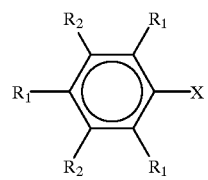

where X is a halogen;
where at least one $R_1$ constituent is an electron withdrawing radical and the remaining $R_1$ constituents are the same or different and are selected from the group consisting of hydrogen and hydrocarbyl radicals having from 1 to about 10 carbon atoms per radical;
where said $R_2$ constituents are selected from the group consisting of hydrogen and hydrocarbyl radicals having from 1 to about 10 carbon atoms per radical;
wherein the contaminated N-methyl-2-pyrrolidone contains at least one contaminant selected from the group consisting of phenol, thiophenol and phenyl disulfide;

2) heating said first stream to a temperature in the range of about 100° C. to about 300° C.; and 3) separating said first stream to produce a NMP-rich stream and a NMP-lean stream;
wherein said NMP-rich stream comprises N-methyl-2-pyrrolidone; and
wherein said NMP-lean stream comprises reaction products of said contaminant, said monohalogenated aromatic compound, and said base.

2. A process according to claim 1 wherein at least one electron withdrawing radical is selected from the group consisting of:

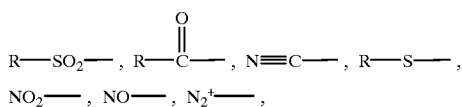

where R is selected from the group consisting of hydrocarbyl radicals having from 1 to about 20 carbons atoms per radical.

3. A process according to claim 2 wherein the amount of said monohalogenated aromatic compound contacted with the contaminated NMP ranges from about 1 mole per mole of said contaminant to about 5 moles per mole of said contaminant.

4. A process according to claim 3 wherein the amount of base to be used ranges from about 0.9 moles per mole of said contaminant to about 3 moles per mole of said contaminant.

5. A process according to claim 4 wherein said monohalogenated aromatic compound is selected from the group consisting of 4-chlorophenylsulfone, 4-chlorophenylbiphenylsulfone, 2-chlorophenylsulfone, 4-chlorobenzonitrile, 4-chlorobenzophenone, and p-nitrochlorobenzene.

6. A process according to claim 5 wherein the amount of said monohalogenated aromatic compound contacted with the contaminated NMP ranges from about 1 mole per mole of said contaminant to about 3 moles per mole of said contaminant.

7. A process according to claim 6 wherein said contaminated NMP is generated from the production of P(AS).

8. A process according to claim 7 wherein contact time for the monohalogenated aromatic compound, base, and contaminated NMP ranges from about 1 minute to about 10 hours.

9. A process according to claim 8 wherein said heating of said first stream is conducted at a temperature in the range of about 150° C. to about 270° C.

10. A process according to claim 9 wherein said separating is effected by distillation.

* * * * *

UNITED STATES PATENT AND TRADEMARK OFFICE
CERTIFICATE OF CORRECTION

PATENT NO. : 6,051,720

DATED : April 18, 2000

INVENTOR(S) : Jon F. Geibel and Richard A. Green

It is certified that error appears in the above-identified patent and that said Letters Patent is hereby corrected as shown below:

In the ABSTRACT, line 1, delete "moving" and insert --- removing --- therefor.

In the ABSRACT, last line, delete "contaminate" and insert --- contaminated --- therefor.

Signed and Sealed this

Twenty-fourth Day of April, 2001

Attest:

NICHOLAS P. GODICI

Attesting Officer

Acting Director of the United States Patent and Trademark Office